United States Patent

Pennaneac'h et al.

[11] Patent Number: 5,207,659
[45] Date of Patent: May 4, 1993

[54] DEVICE FOR DISPENSING DROPS OF SMALL VOLUME, IN PARTICULAR FOR OPHTHALMOLOGICAL CARE

[75] Inventors: Hervé Pennaneac'h; Michel Theot, both of Verneuil-sur-Avre; Claude Jouillat, Montigny-sur-Avre, all of France

[73] Assignee: Société Technique de Pulvérisation - S.T.E.P., Verneuil-sur-Avre, France

[21] Appl. No.: 861,579

[22] Filed: Apr. 1, 1992

[30] Foreign Application Priority Data

Apr. 5, 1991 [FR] France .................. 91 04178

[51] Int. Cl.$^5$ .................................. A61M 35/00
[52] U.S. Cl. ..................... 604/298; 604/300; 417/489; 222/340; 222/387; 222/494
[58] Field of Search ............ 604/294, 295, 298, 300, 604/301, 302; 417/489; 222/340, 387, 494

[56] References Cited

U.S. PATENT DOCUMENTS

| | | | |
|---|---|---|---|
| 4,623,337 | 11/1986 | Maurice | 604/298 |
| 4,930,999 | 1/1990 | Brunet et al. | 417/552 |
| 5,024,355 | 6/1991 | Jouillat et al. | 222/162 |

Primary Examiner—Randy C. Shay
Attorney, Agent, or Firm—Sughrue, Mion, Zinn, Macpeak and Seas

[57] ABSTRACT

A device for dispensing of small volume comprises a pump associated with a container of the substance to be dispensed, the pump comprising: a hollow pump body; and a piston sliding inside said pump body in sealing contact with the pump body around a circular periphery of diameter D2; wherein the pump further includes: a push rod including a central channel in which a valve seat is formed, the push rod sliding in contact with the pump body around a circular periphery of diameter D1 less than D2; a punch secured to the piston and capable of bearing in sealed manner against the valve seat; and resilient means urging the piston against the valve seat.

7 Claims, 8 Drawing Sheets

DEVICE FOR DISPENSING DROPS OF SMALL VOLUME, IN PARTICULAR FOR OPHTHALMOLOGICAL CARE

The present invention relates to a device for dispensing drops of small volume, in particular for ophthalmological care. More particularly, the device of the invention makes it possible to dispense drops of a liquid or a milk into the eye of a patient, the volume of the drops being of the order of 10 microliters, for example.

BACKGROUND OF THE INVENTION

Devices of this type are known in the state of the art. Thus, Document FR 2 640 589 describes a metering pump for dispensing small-volume drops, the pump comprising a pump body having an open end communicating with a container of the substance to be dispensed, and an end provided with an end wall pierced by a central orifice. A piston secured to a push rod slides in sealed manner inside the pump body, while the push rod slides through the central orifice in the end wall of the pump body. Said push rod includes a central channel opening out axially to the outside of the pump, and radially in the vicinity of the piston into a pump chamber which is delimited by the piston and the pump body, said pump chamber extending between the piston and the end wall of the pump body. The outside end of the central channel in the rod is provided with an outlet valve which may be in the form of two hemispheres that are connected together by a resilient spacer. In addition, a return spring applies resilient thrust to the push rod, thereby urging the piston towards the end wall of the pump body. When a user presses on the push rod, generally via a pusher, the piston is pushed into the container of substance until it leaves the pump body: so long as the piston has not left the pump body, this movement sets up suction in the pump chamber because the outlet valve remains closed; when the piston leaves the pump body, a measured quantity of substance is sucked into the pump chamber. When the user releases the push rod, the piston is returned towards the end wall of the pump by the return spring, and as a result the substance contained in the pump chamber is compressed and ejected via the central channel of the push rod and via the outlet valve which opens under the effect of applied pressure.

Such metering pumps nevertheless suffer from the drawback that the outlet valve is a very small part which is quite difficult to make and to assemble, thereby significantly increasing the cost of the pump. Similarly, the fact that the push rod includes an axial channel and a radial channel means that it must be molded in a special mold including a sliding pin. Such molds are expensive and relatively fragile and thus have an unfavorable influence on the cost of the pump. Since such pumps are designed to be discarded once their container of substance has been emptied, it is appropriate to minimize the cost thereof.

An object of the present invention is to provide a device for dispensing drops of small volume while avoiding the above-mentioned drawbacks.

SUMMARY OF THE INVENTION

The present invention thus provides a device for dispensing drops of small volume, the device comprising a pump associated with a container of substance to be dispensed, said pump comprising:

a hollow pump body extending between a first end close to the container and a second end closed by an end wall which is pierced by a central opening, said pump body including a passage between its inside and the container; and a piston sliding inside said pump body in sealing contact with said pump body around a circular periphery having a first diameter D2, thereby isolating the container from a pump chamber inside the pump body, said piston being slidable towards the container to a position in which it puts said pump chamber into communication with the container via said passage;

wherein the pump further includes:

a push rod including a central channel in which a valve seat is formed, said push rod sliding through said central opening in the end wall of the pump body, and said push rod being in contact with the pump body around a circular periphery having a second diameter D1 that is smaller than said first diameter D2;

a punch secured to the piston and extending along said central channel of the push rod and being suitable for bearing in sealed manner against the valve seat;

support means secured to the pump body and disposed at the end thereof adjacent to the container; and resilient means bearing against the support means and urging the piston towards the end wall of the pump body.

The resilient means may be disposed inside a spring chamber isolated from the container and delimited by: the support means; a cylindrical wall secured to said support means; and a portion of the piston sliding in sealing contact with said cylindrical wall when the piston slides in the pump body. In a variant, the resilient means may be disposed at an end of the container distant from the piston, in which case said resilient means is isolated from said container by a partition, and slides in sealed manner through the partition.

Advantageously, the container includes a cylindrical wall through which a piston slides freely, or else said container includes a deformable wall, in such a manner that the volume of said container reduces as the substance it contains is consumed.

The device of the invention may further include an eyepiece adapted to be pressed around the periphery of the eye of a user so as to adjust the distance between the eye and an outlet end of said device, and in such a manner as to center the device relative to the eye.

In a particular embodiment of the invention, the pump body includes a first cylindrical wall close to the container of substance, said first cylindrical wall having the diameter D2 and receiving the piston, and a second cylindrical wall close to the end wall of said pump body, said second cylindrical wall having a diameter D1 smaller than the diameter D2, and a radial flange of the push rod slides in sealed manner inside said second cylindrical wall.

BRIEF DESCRIPTION OF THE DRAWINGS

Embodiments of the invention are described by way of example with reference to the accompanying drawings, in which.

DETAILED DESCRIPTION

Figure 1:
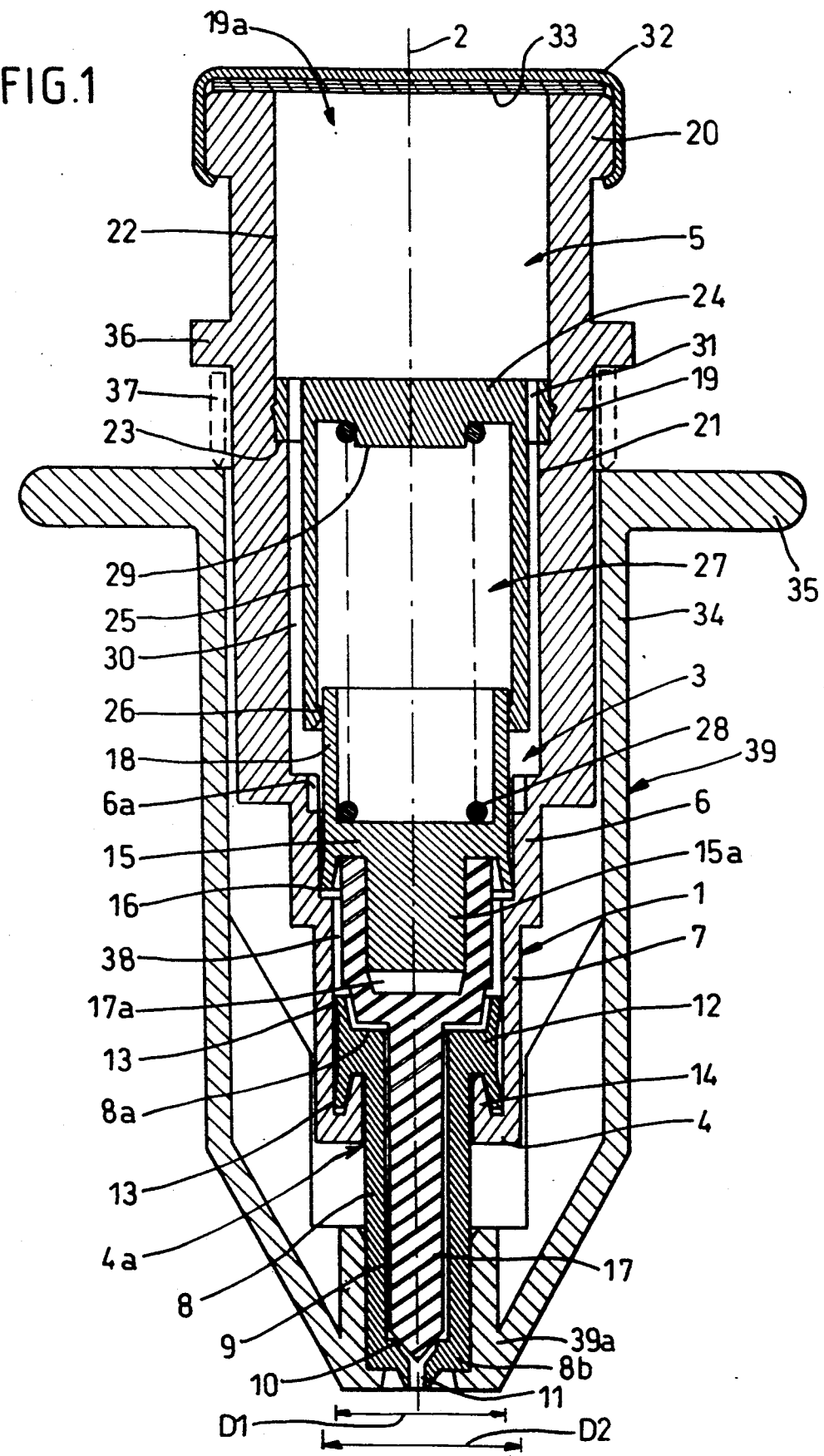
FIG. 1 is a section view through a first embodiment of the device of the invention in a rest position.
Figure 2:
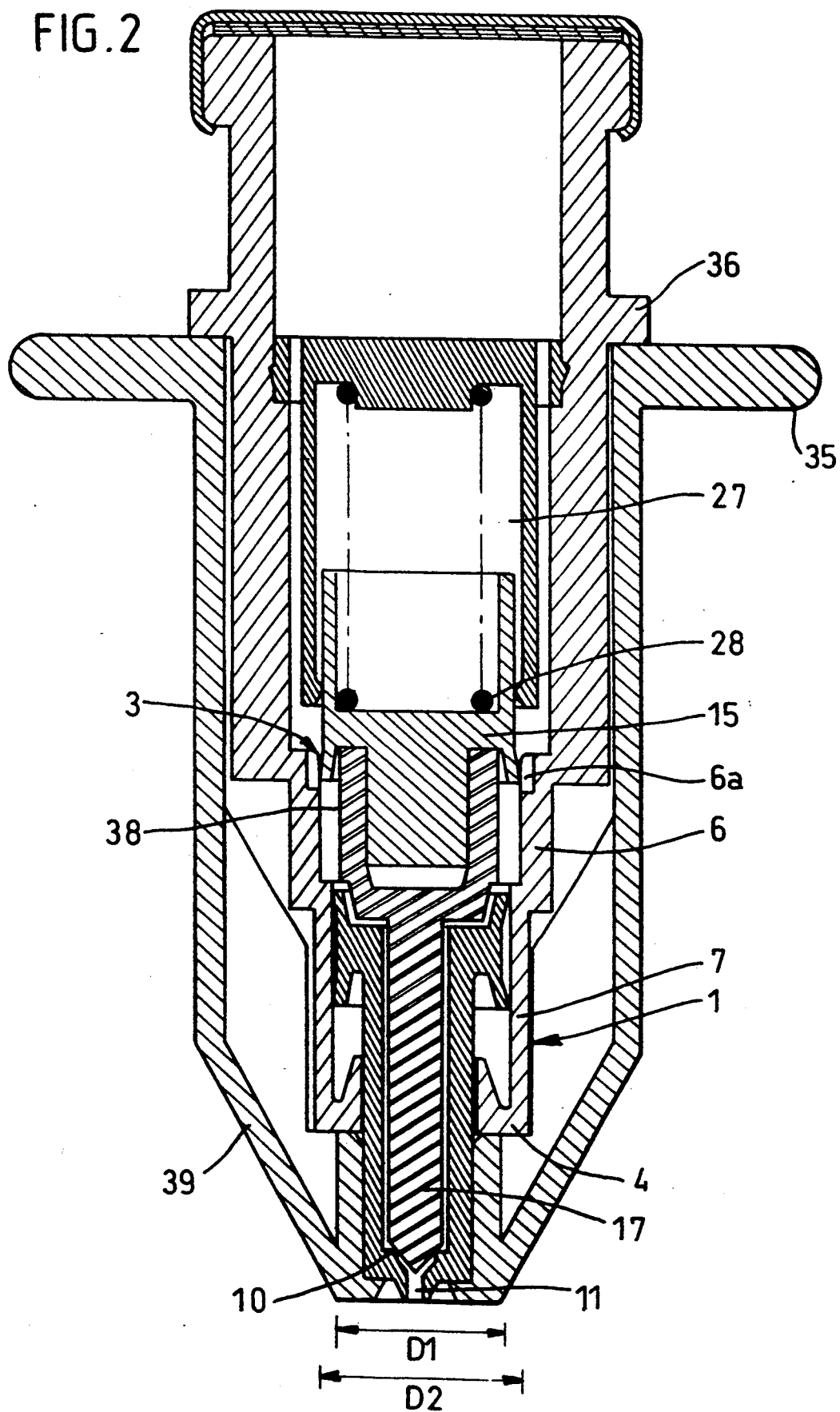
FIG. 2 is a section view of the FIG. 1 device in a pump chamber filling position.

First embodiment (FIGS. 1 and 2)

With reference to FIG. 1, the device for dispensing drops of small volume in a first embodiment of the invention comprises a metering pump associated with a container 5 of substance to be dispensed.

The metering pump comprises a hollow pump body 1 which may be made of molded plastic and which has an axis of revolution 2. The pump body 1 extends between an open first end 3 in communication with the container 5 for the substance, and a second end which is closed by an end wall 4 that is pierced by a central opening 4a. In the particular embodiment shown in FIG. 1, the pump body 1 comprises a first cylindrical wall 6 close to the open end 3 and having a relatively large inside diameter D2, and a second cylindrical wall 7 close to the end wall 4 and having a smaller inside diameter D1. The cylindrical wall 6 further includes internal fluting 6a extending axially over a certain distance from the open end 3 of the pump body.

A push rod 8 comprising a body of revolution about the axis 2 and that may be made of molded plastic is slidably received in the central opening 4a of the end wall 4. The push rod 8 extends between an inside end 8a inside the pump body and an outside end 8b outside the pump body. The push rod 8 includes a central channel 9 which extends from the inside end 8a to a constriction 10 constituting a valve seat, and it extends to the outside end 8b via a short central outlet channel 11 of small diameter. In this particular example, the push rod 8 slides through the opening 4a without sealing, and the inside end 8a of the said push rod is formed with an outwardly directed flange 12 which extends to the vicinity of the small diameter cylindrical wall 7 and which includes at least one peripheral sealing lip 13 (and preferably two lips) in sealing contact with the cylindrical wall 7. Advantageously, a ring 14 surrounding the opening 4a extends a certain distance into the pump body 1 from the end wall 4. Thus, as described below, when the flange 12 is urged towards the end wall 4, the ring 14 serves as an abutment for said flange 12 and prevents one of the sealing lips 13 coming into abutment against the end wall 4, which could damage said sealing lip.

The metering pump also includes a piston 15 sliding inside the cylindrical wall 7 of the pump body 1. The piston 15 may be made of molded plastic and it is a body of revolution about the axis 2. It includes at least one peripheral sealing lip 16 in sealing contact with the cylindrical wall 7. The piston 15 is secured to a punch 17 that is a body of revolution about the axis 2 and that may be made of molded plastic. The punch extends along the central channel 9 of the push rod to the valve seat 10, and it may be pressed in sealed manner against said valve seat 10. In this particular example, the piston 15 and the punch 17 are two separate pieces: the punch 17 includes an axial blind cylindrical cavity 17a that is open towards the piston 15, and the piston 15 includes a cylindrical portion 15a of complementary shape that is a force fit in the cavity 17a. By making the piston 15 and the punch 17 as two pieces, it is possible to use two materials of different characteristics for the piston and the punch, e.g. a material that is relatively flexible to the piston and a material that is relatively rigid for the punch. Nevertheless, the piston and the punch could be made as a single piece without going beyond the ambit of the present invention. In this particular example, the piston 15 also includes a peripheral skirt 18 that extends towards the container of substance 5 for a purpose described below. The pump body 1 thus co-operates with the piston 15, the push rod 8, and the punch 17 to define a pump chamber 38.

The container 5 comprises an enclosure in the form of a cylindrical side wall integrally molded with this case with the pump body 1, and extending from the open end 3 of said pump body to an open end 19a provided with an outwardly directed flange 20. As shown in FIG. 1, the cylindrical wall 19 includes a first portion 21 close to the open end 3 of the pump body having an inside diameter greater than the inside diameter of the cylindrical 7 of the pump body, and a second portion 22 defining the container 5 close to the flange 20, having a larger inside diameter and separated from the portion 21 by a shoulder 23.

A disk of plastic 24 whose outside diameter is equal to the inside diameter of said second portion 22 is disposed inside the second portion 22 of the container 5 in abutment against the shoulder 23, and is fixed to the cylindrical wall 19 by any conventional means, e.g. by snap-fastening between a peripheral outside lip of said disk in a peripheral inside groove of the portion 22 of the wall 19. A cylindrical sleeve 25 extends from the disk 24 to the vicinity of the open end 3 of the pump body and it is engaged over the skirt 18 of the piston 15 in such a manner as to enable said skirt 18 to slide inside said sleeve 25 in sealing contact with said sleeve. Advantageously, the sleeve 25 includes an inside peripheral sealing lip 26 that bears resiliently against the skirt 18. In a variant, the sealing lip 26 could be formed on the outside of the skirt 18. Similarly, the sleeve 15 could engage inside the skirt 18 instead of outside, without going beyond the ambit of the present invention.

The disk 24, the sleeve 25, the piston 15, and the skirt 18 thus constitute a sealed enclosure or "spring box" isolating a spring chamber 27 which is filled with air or some other gas and which contains a spring 28, e.g. a coil spring, disposed between the disk 24 and the piston 15 so as to urge the piston 15 resiliently towards the end wall 4 of the pump body. The punch 17 secured to the piston 15 is thus resiliently pressed against the valve seat 10, thereby urging the push rod 8 towards the end wall 4 while the flange 12 on said push rod 8 is in abutment against the ring 14 on the end wall 4. The disk 24 may optionally include a central projection 29 facing the piston 15 for the purpose of centering the spring 28. This disposition is particularly advantageous when the spring 28 is made of metal and the substance contained in the container 5 is sensitive to pollution, in particular from heavy metals that may be contained in the spring, or if said substance is liable to oxidize the spring: since the spring 28 is isolated inside its spring chamber, it cannot interact with the substance to be dispensed.

The outside diameter of the cylindrical sleeve 25 is perceptibly less than the inside diameter of the first portion 21 of the cylindrical wall 19, thereby leaving free an annular passage 30 between the sleeve 25 and the cylindrical wall 19, said annular passage 30 communicating with the fluting 6a at the open end 3 of the pump body. In addition, the disk 24 includes a plurality of axial passages 31 that put the annular passage 30 into communication with the remainder of the container of substance 5.

The container 5 is closed by a cover, e.g. a metal capsule 32 crimped over the flange 20. Advantageously, a disk-shaped flat gasket 33 is interposed between the container 5 and the metal capsule 32 so as to close the container in sealed manner and so as to prevent any contact between the metal capsule 32 and the substance contained in the container 5.

Finally, a pusher 39 that is a body of revolution about the axis 2 and that may be made of molded plastic is engaged on the push rod 8. The pusher 39 may comprise a peripheral side wall 34 surrounding the pump body 1 and a portion of the container 5, extending from an outlet end 39a close to the outside end 8b of the push rod 8 to an outwardly-projecting thrust flange 35. The wall 19 may include an outwardly projecting collar 36 suitable for acting as an abutment against the flange 35 when the device is actuated, as described below. The pusher 39 may optionally be provided with safety means such as a tamperproofing ring 37, for example (shown in dashed lines in FIG. 1), integrally molded with the pusher and disposed between the thrust flange 35 of the pusher and the abutment collar 36, which ring must be torn off before the device can be actuated. The wall 19 may optionally include outwardly projecting studs (not shown), and the wall 34 of the pusher may include complementary slots (not shown) so that the device cannot be actuated without the studs being brought into alignment with the slots by rotating the pusher about the axis 2, thereby preventing the device from being actuated involuntarily.

None of the plastic parts of the device as described above requires a mold with moving pins. In addition, the device is quite simple to assemble: the following are placed successively inside the pump body 1: the push rod 8; the punch 17 as previously assembled with the piston 15; the disk 24 together with the spring 28; and then the pusher 39 is engaged on the push rod 8. The device can then be stored over a period of time before the container 5 is filled with the substance to be dispensed, and is closed by means of the capsule 32 and the gasket 39.

The device operates as follows: when a user presses against the capsule 32, i.e. moves the thrust flange 35 towards the abutment collar 36 as shown in FIG. 2, the push rod 8 is displaced towards the open end 3 of the pump body and takes both the punch 17 and the piston 15 with it. Because the sealing contact diameter D1 between the push rod 8 and the pump body is smaller than the sealing contact diameter D2 between the piston 15 and said pump body, the volume of the pump chamber 38 increases. During this movement, suction is thus established inside the pump chamber 38, thereby urging the piston 15 towards the push rod 8 and thus reinforcing the force with which the punch 17 is pressed in sealed contact against the valve seat 10. This suction increases until the sealing lip 16 of the piston 15 comes level with the fluting 6a, as shown in FIG. 2. At that moment, the pump chamber 38 is put into communication with the annular passage 30 and thus with the container 5 via the fluting 6a, thereby causing a quantity of substance to be sucked into the pump chamber 38. The same result could be obtained without fluting 6a, providing the stroke of the piston is sufficient for the sealing lip 16 to disengage from the pump body and enter the container 5 when the container 5 is pushed home until the abutment collar 36 engages the flange 35 on the pusher, in which case the pump chamber 38 communicates with the container 5 via its open end 3.

It may be observed that to ensure that the quantity of substance is sucked into the pump chamber 38, the device must be placed substantially vertically, or in any event it must be inclined, so that the pump body 1 is beneath the container 5 so that the substance contained in the container 5 is in the vicinity of the open end 3 of the pump body under gravity.

During this movement, the spring 28 is compressed and the volume of the spring chamber 27 decreases, thereby causing the gas contained therein to be compressed as well, thus adding gas pressure to the force of the spring 28.

When the user releases the container 5, it is returned upwards together with the pump body 1 under drive from the spring 28 and possibly from the gas compressed in the spring chamber 27. In other words, the piston 15 moves inside the pump body 1 towards the end wall 4 of the pump body, pushing the push rod 8 with it via the punch 17. Because the sealing contact diameter D1 between the push rod 8 and the pump body 1 is smaller than the sealing contact diameter D2 between the piston 15 and said pump body, the volume of the pump chamber 38 decreases during this movement, thereby compressing the substance contained in said pump chamber. This compression tends to move the push rod and the piston apart, and thus to lift the punch 17 off the valve seat 10: the quantity of substance contained inside the pump chamber 38 is thus expelled into the central channel 9 and into the outlet channel 11.

In general, this quantity is very small, being of the order of about 10 microliters, such that it is expelled in the form of a drop of small volume. If L is the working stroke of the piston 15, i.e. its stroke during which the pump chamber 38 is not in communication with the container 5, then the volume V of the expelled quantity of fluid is given by the following equation:

$$V = L\pi(D2^2 - D1^2)/4$$

A pump of the invention thus makes it easy to obtain an expelled volume that is small, merely by ensuring that the sealing contact diameter D1 between the push rod 8 and the pump body 1 is close enough to the sealing contact diameter D2 between the piston 15 and the pump body 1. In the example shown in FIGS. 1 and 2, this is achieved by splitting the pump body 1 into two cylindrical portions 6 and 7 of diameters D2 and D1 that are relatively close, D1 being smaller than D2, and by making the piston secured to the punch slide inside the portion of larger diameter D2, while a second piston (constituted by the flange 12 and its sealing lips 13) secured to the push rod slides inside the portion of smaller diameter D1. The same result could be obtained without going beyond the ambit of the invention by using a pump body 1 of uniform inside diameter D2 in which the piston 15 slides, and by providing sealing between the push rod 8 and the pump body 1 at the central opening 4a, in which case the diameter D1 is the diameter of the opening 4a. To ensure that the volume of the expelled quantity is small, it is necessary merely that D1 should be quite close to D2, i.e. that the opening 4a and the push rod 8 should be rather wide.

At the end of the return movement of the piston 15 and of the push rod, the device is in the position shown in FIG. 1 where the flange 12 on the push rod 8 is in abutment against the ring 14 and where the punch 17 is pressed in sealed manner against the valve seat 10.

It is advantageous for the valve seat 10 to be disposed in the immediate vicinity of the outside end 8b of the push rod as shown in FIG. 1. This minimizes the volume of substance contained in the outlet channel 11 where the substance is in contact with ambient air between two successive utilizations of the device, i.e. where the substance is subjected to drying, to oxidization, and to various kinds of pollution. Nevertheless, the valve seat could be further away from the end 8b without thereby going beyond the present invention.

It may be observed that the quantity of substance taken out of the container 5 is not compensated by a corresponding intake of air: the pressure inside the container 5 thus decreases a little each time the substance it contains is consumed. In order to limit this drop in pressure to a value that is compatible with operation of the metering pump of the device of the invention, the container 5 should not be completely filled with the substance, but should also contain air or preferably an inert gas such as nitrogen. Advantageously, the gas is originally injected into the container 5 at a certain overpressure, thereby providing a corresponding reduction in the underpressure that exists inside the container 5 after all of the substance to be dispensed has been consumed.

FIGS. 3 to 9 show variants of the device of the invention, all of which operate on the same principle as the device shown in FIGS. 1 and 2. In the description below of those figures, portions that are identical or similar to portions in FIGS. 1 and 2 are designated by the same references as in FIGS. 1 and 2, and only the differences are described in detail.

Figure 3:
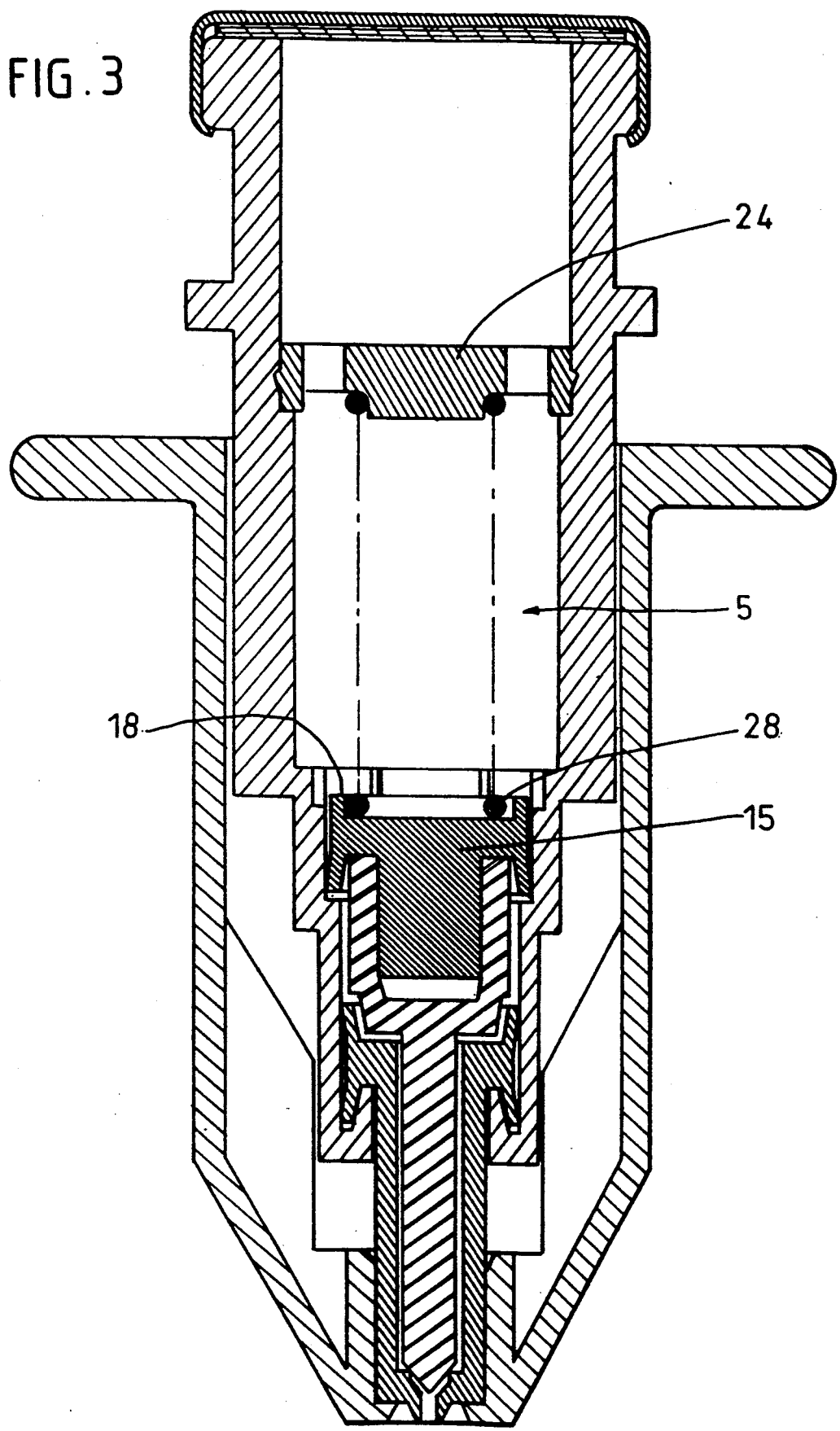
FIG. 3 is a section view through a second embodiment of the device of the invention.

Second embodiment (FIG. 3)

FIG. 3 shows an embodiment of the device of the invention suitable for use with a substance to be dispensed that is not harmed by coming into contact with metal. In this embodiment, the sleeve 25 of the disk 24 is omitted and the skirt 18 of the piston is reduced to the bare minimum required for centering the spring 28 on the piston 15, as shown in FIG. 3. The spring 28 is then immersed in the substance to be dispensed from the container 5.

Figure 4:
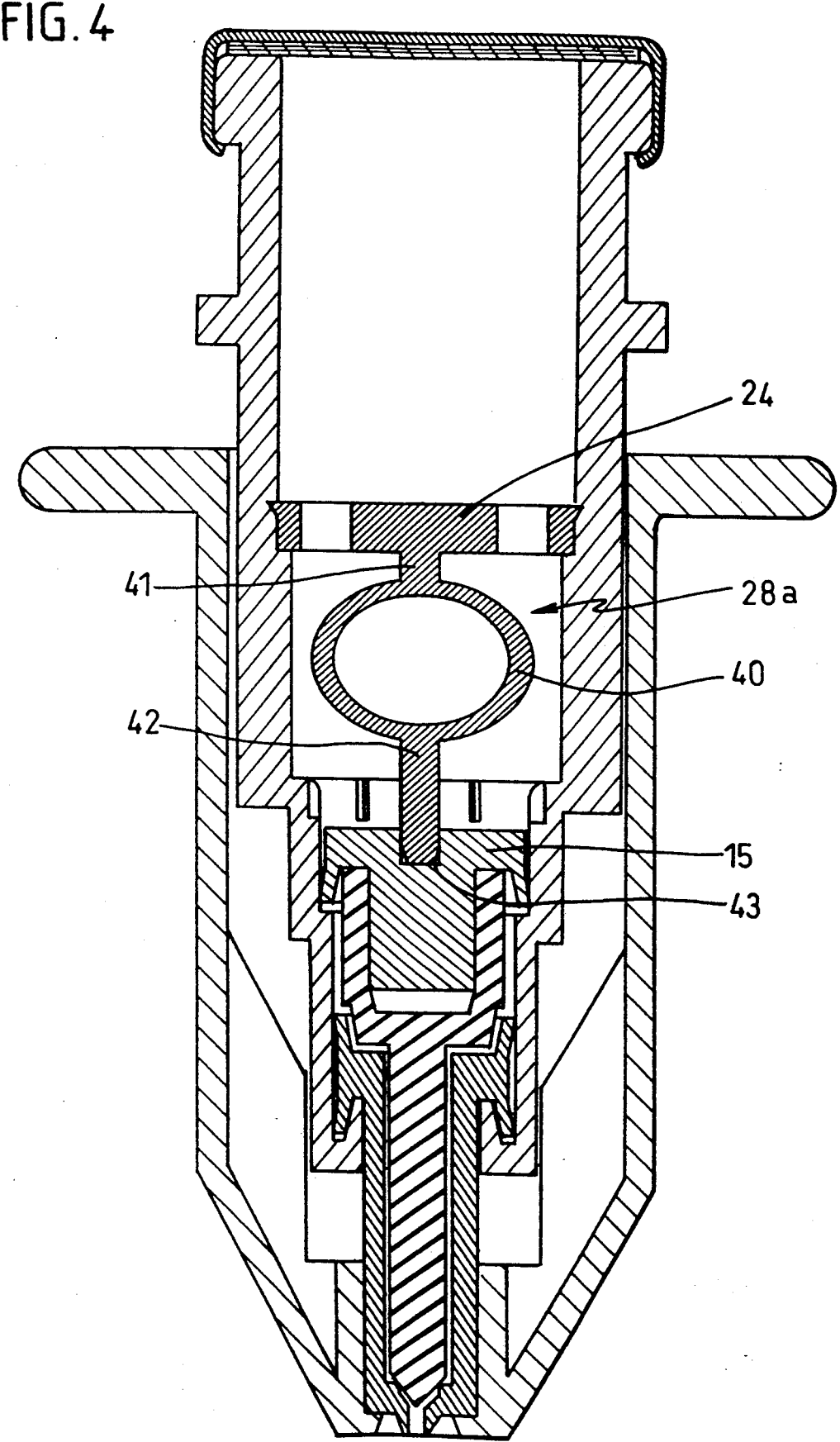
FIG. 4 is a section view through a third embodiment of the device of the invention.

Third embodiment (FIG. 4)

FIG. 4 shows another embodiment of the device of the invention, similar to that of the FIG. 3, but in which the metal spring 28 is replaced by a spring 28a made of plastic, and which may therefore be immersed in the substance contained in the container 5 even if said substance is fragile. In the example shown in FIG. 4, the plastic spring 28 is in the form of a ring 40 that is resiliently deformable in the axial direction. The ring 40 is connected to the support disk 24 by a short first peg 41 integrally formed with the support disk 24, and the ring 40 extends axially towards the piston 15 by means of a second peg 42 that penetrates into a centering recess 43 formed in the piston 15. In this particular embodiment, the skirt 18 on the piston 15 is completely omitted.

Figure 5:
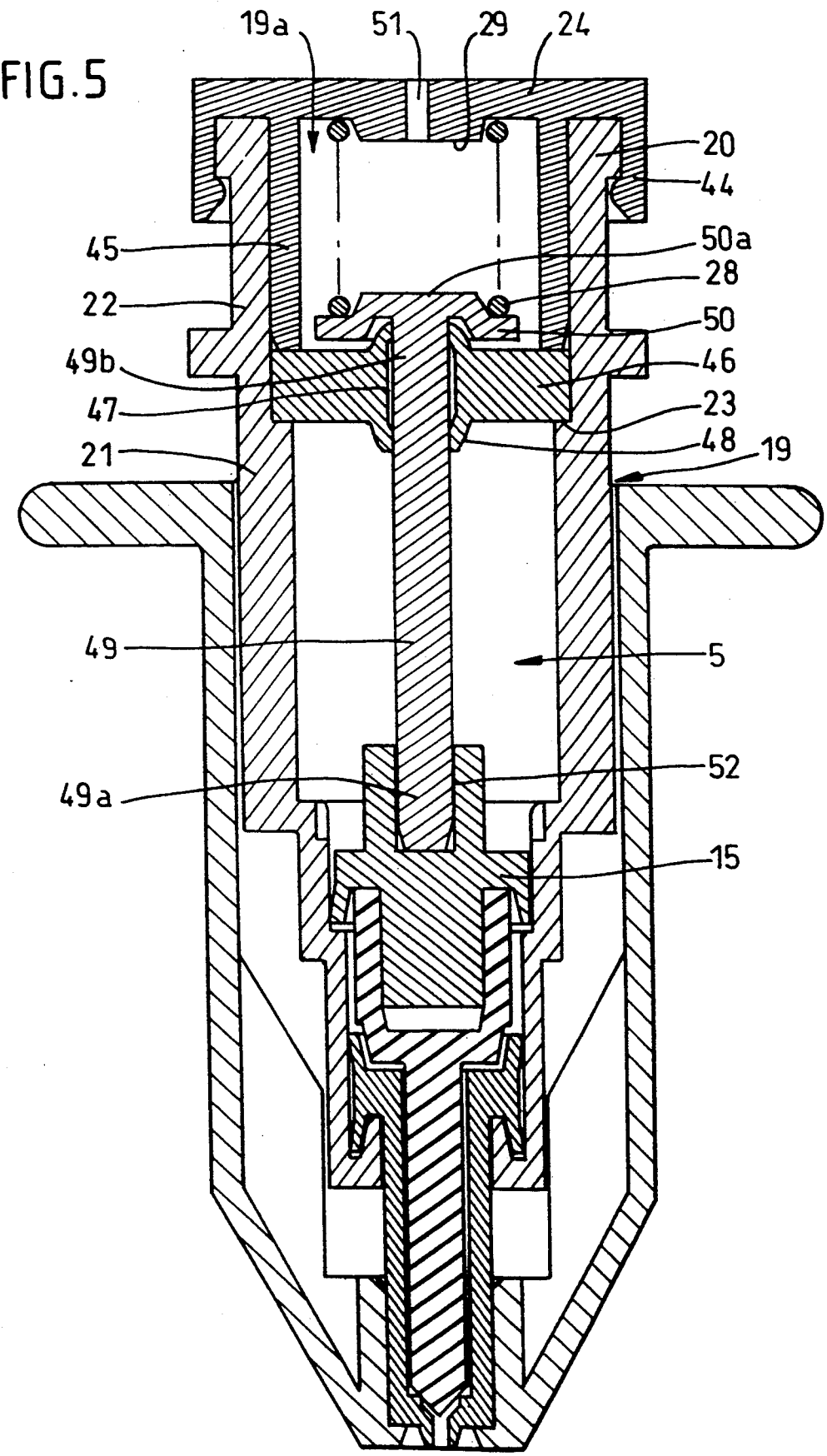
FIG. 5 is a section view through a fourth embodiment of the device of the invention.

Fourth embodiment (FIG. 5)

In the embodiment shown in FIG. 5, the disk 24 supporting the spring 28 is fixed at the open end 19a of the enclosure 19. The support disk 24 is extended axially towards the pump body 1 by an outside skirt 44 which snaps over the flange 20, and by an inside peripheral skirt 45 which extends inside the second portion 22 of the enclosure 19 to the vicinity of the shoulder 23. A ring 46 of outside diameter equal to the inside diameter of the second cylindrical portion 22 of the enclosure 19 is disposed in sealing contact with said second cylindrical portion 22, in abutment against the shoulder 23, and it is locked in place by the inside skirt 45. The ring 46 is pierced by a central orifice 47 provided with inside sealing lips 48, and a rod 49 slides through said orifice 47 in sealing contact with the sealing lip 48. The container 5 of substance extending between the ring 46 and the pump body 1 is thus isolated from the outside. The rod 49 extends between a first end 49a in contact with the piston 15 and a second end 49b situated between the ring 46 and the support 24 and including a bearing surface 50 for the spring 28, said spring being disposed between said bearing surface 50 and the support disk 24. The support disk 24 advantageously includes the above-described spring-centering projection 29, and the bearing surface 50 may include a similar projection 50a facing the projection 29. The support disk 24 may also include a vent 51 for preventing air being compressed when the rod 49 slides through the orifice 47. The first end 49a of the rod 49 is preferably centered on the piston 15, e.g. by engaging in a cavity 52 of the piston 15.

The end 49a of the rod 49 is advantageously a force fit in the cavity 52 of the piston 15 so as to avoid any decoupling between the rod 49 and the piston 15.

Thus, as before, the piston 15 is urged towards the end wall 4 of the pump body 1 by the spring 28, but in this case by means of the rod 49.

Figure 6:
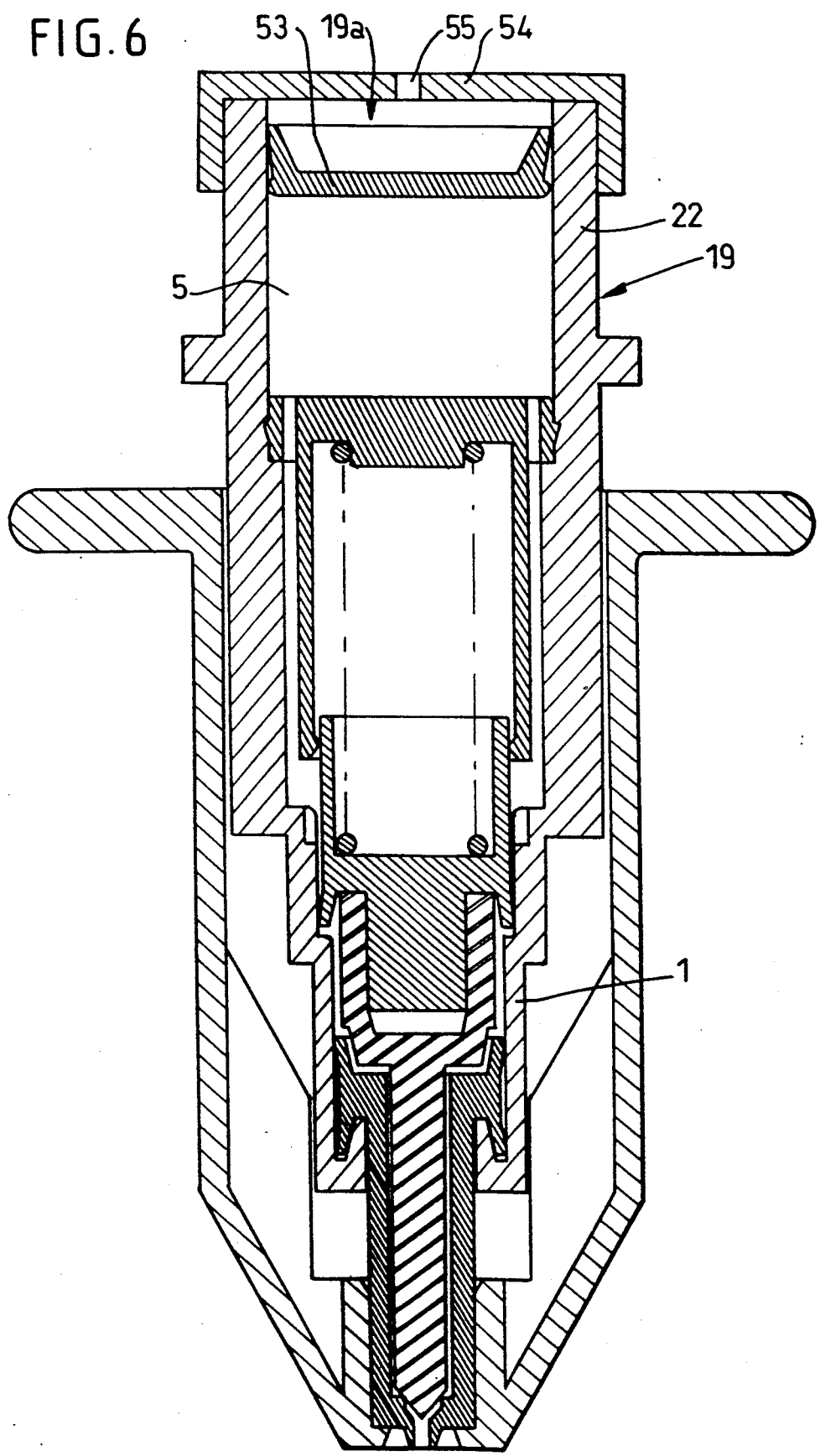
FIG. 6 is a section view through a fifth embodiment of the device of the invention.

Fifth embodiment (FIG. 6)

FIG. 6 shows a device similar to that of FIGS. 1 and 2 in which the open end 19a of the enclosure 19 of the container is no longer closed by a crimped metal capsule, but by a piston 53 that is capable of sliding axially in sealing contact with the second cylindrical portion 22 of the enclosure 19. The piston 5 thus moves towards the pump body 1 as the substance contained in the container 5 is consumed, such that the inside volume of said container decreases and the underpressure in said container 5 is eliminated or is restricted to a negligible value. The open end 19a may be covered by a cover 54 provided with a vent 55, thereby avoiding suction being set up behind the piston 53 when the piston moves towards the pump body 1.

Figure 7:
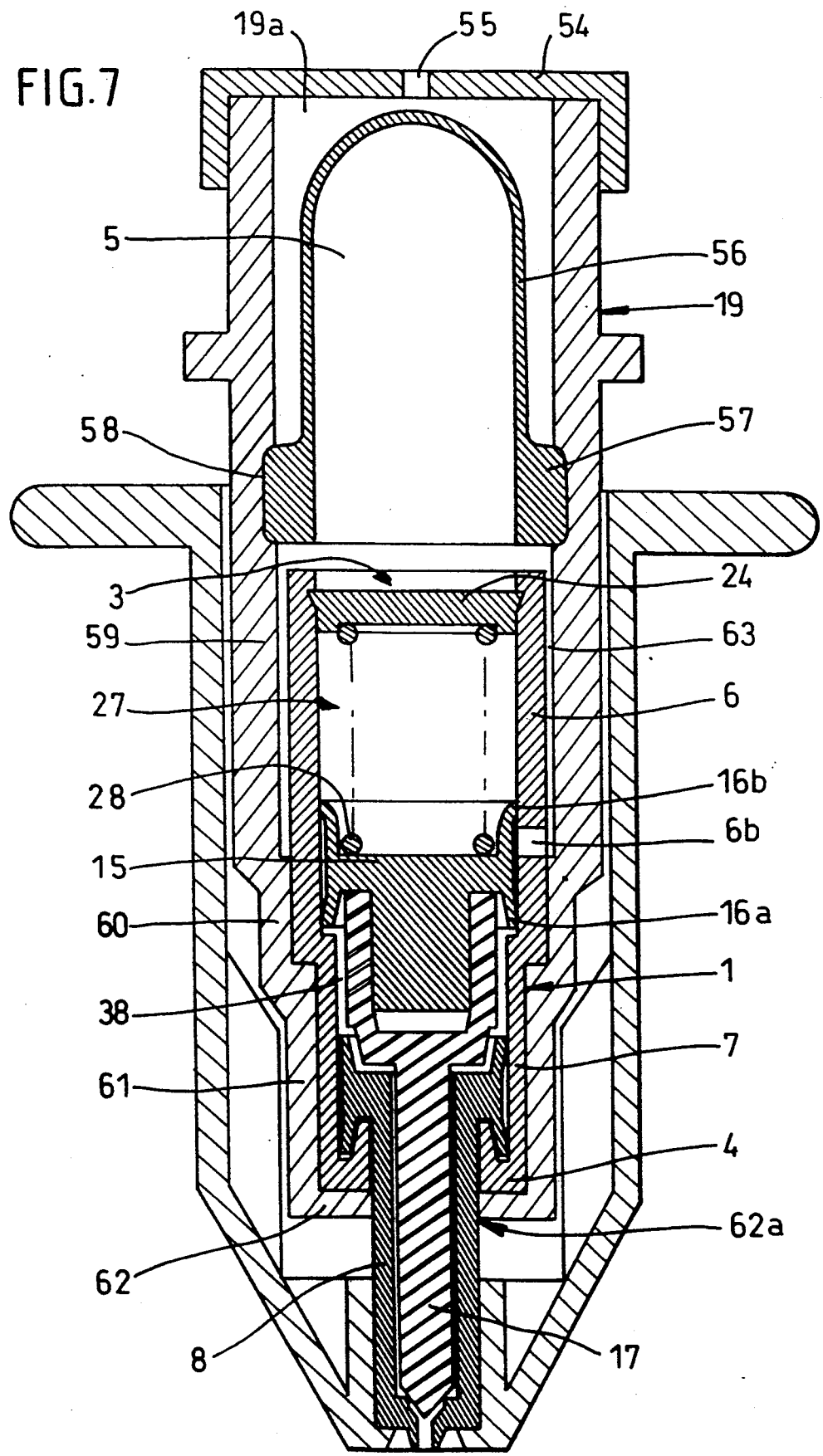
FIG. 7 is a section view through a sixth embodiment of the device of the invention.

Sixth embodiment (FIG. 7)

FIG. 7 shows another variant of the device of the invention in which the container 5 is delimited by a rigid enclosure 19 and by a deformable wall 56 constituting a flexible bag that enables the volume of the container 5 to decrease as the substance it contains is consumed while avoiding any underpressure in the container 5, or at least limiting it. The deformable wall 56 may be fixed to the wall 19 by any conventional means: for example it may include a relatively thick and thus fairly rigid peripheral ring 57 snapped into a complementary peripheral inside groove 58 in the enclosure 19. As in the example of FIG. 6, the open end 19a of the enclosure 19 may be closed by a cover 54 provided with a vent 55.

In other respects the device may be similar to that shown in FIG. 1. However, in the example of FIG. 7, the enclosure 19 is not integrally molded with the pump body 1, but constitutes a part that is separate from the pump body. Going from its open end 19a, the enclosure 19 includes a first cylindrical wall 59 of inside diameter greater than the outside diameter of the first cylindrical wall 6 of the pump body 1, followed by a second cylindrical wall 60 of inside diameter equal to the outside diameter of said cylindrical wall 6 of the pump body, and then a third cylindrical wall 61 of inside diameter equal to the outside diameter of the second cylindrical wall 7 of the pump body. Said third cylindrical wall 61 extends radially inwards in the form of an annular end wall 62 defining a central orifice 62a.

The pump body 1 is a force fit inside the walls 60 and 61 of the enclosure 19 such that the end wall 4 of said pump body is placed substantially in abutment against the end wall 62 of the enclosure 19 and the push rod 8 passes through the central orifice 62a. The first cylindrical wall 6 of the pump body 1 extends inside the first cylindrical wall 59 of the enclosure 19 in such a manner as to define an annular passage 63 between said two walls. In addition, the first cylindrical wall 6 of the pump body is pierced by at least one through orifice 6b which communicates with the container 5 via the annular passage 63. The above-described support disk 24 is no longer snap-fastened in the enclosure 19, but instead in the first cylindrical wall 6. In this case, unlike FIG. 1, the support disk 24 has no orifice, thereby hermetically closing the open end 3 of the pump body 1. In addition, the piston 15 has two peripheral sealing lips 16a and 16b in this case respectively constituting a lower lip and an upper lip when the device is in the position in which it is used. At rest, as shown in FIG. 7, the lips 16a and 16b are situated on either side of the orifice 6b. As a result, the pump chamber 38 is isolated from the container 5 by the lower lip 6a, while the upper sealing lip 6b isolates the spring chamber 27 as delimited by the piston 15, the first cylindrical wall 6, and the support disk 24. The above-described spring 28 is disposed inside the spring chamber 27, between the piston 15 and the support disk 24, thereby urging the piston 15 towards the end wall 4 of the pump body 1.

As described above, when the device is actuated, the piston slides initially towards the first end 3 of the pump body, with the spring chamber 27 thus remaining isolated, while the pump chamber 38 is put into communication with the container 5 via the orifice 6b as soon as the lower lip 16a of the piston has gone beyond said orifice 6b, thereby enabling the pump chamber 38 to fill with substance. Thereafter, operation of the pump is the same as described above.

It will be understood that making the pump body 1 and the enclosure 19 as two separate pieces as described above is independent from providing the deformable wall 56, and that such two-piece construction is applicable to the other embodiments of the invention.

Figure 8:
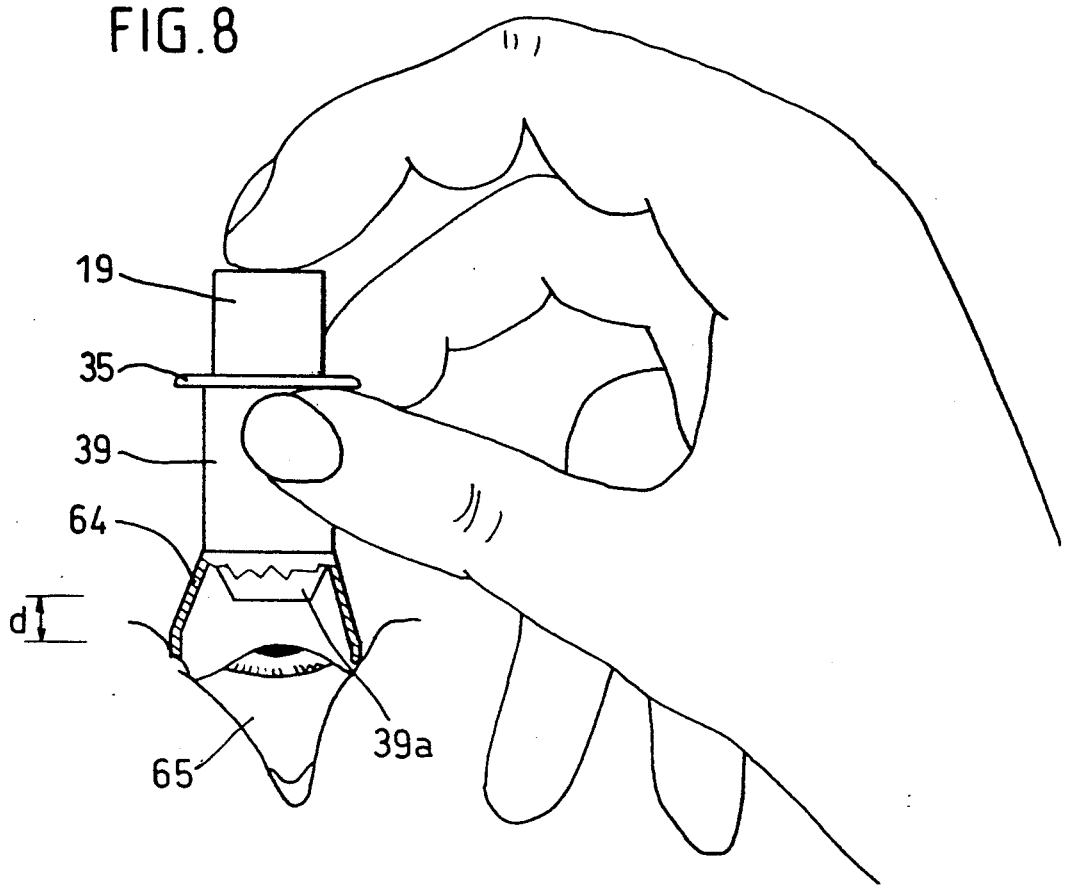
FIG. 8 is a view partially in section showing a seventh embodiment of the device that is fitted with an eye-piece in use.
Figure 9:
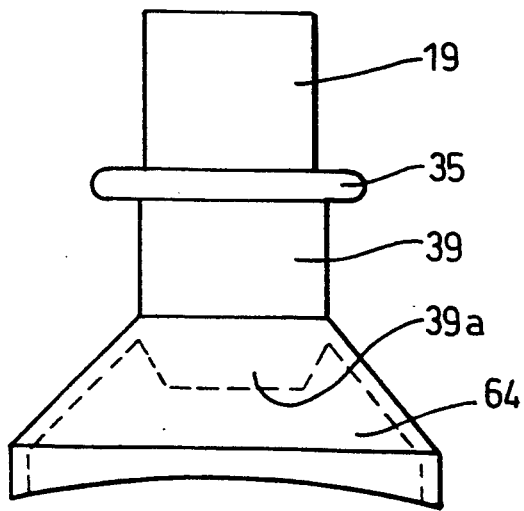
FIG. 9 is an elevation view of the FIG. 8 device.

Seventh embodiment (FIGS. 8 and 9)

FIGS. 8 and 9 show a device as described above (comprising any of the above embodiments or a combination thereof) in association with an eye-piece 64 secured to the pusher 39. The eye-piece 64 may be integrally molded with the pusher 39 or it may be added thereto. The eye-piece 64 may be in the form of a flared peripheral wall extending around the outlet end 39a of the pusher and adapted to be pressed around the eye 65 of the user. The device is thus centered relative to the eye and the distance d between the outlet end 39a of the pusher and the eye 65 of the user is adjusted automatically, thereby enabling drops to be delivered under optimum conditions.

It is recalled that the device of the invention is particularly advantageous in ophthalmological applications, because drops are not emitted when the user presses against the enclosure 19, at which time the user is likely to blink because that is when a drop is expected, but after the user has stopped pressing the device, i.e. at a moment when a drop is not expected and when there is every likelihood of the eyelids being wide open.

We claim:

1. A device for dispensing drops of small volume, the device comprising a pump and a container of substance to be dispensed, said pump comprising:
   a hollow pump body extending between a first end close to the container and a second end closed by an end wall which is pierced by a central opening, said pump body including a passage between its inside and the container; and
   a piston sliding inside said pump body in sealing contact with said pump body around a circular periphery having a first diameter D2, thereby isolating the container from a pump chamber inside the pump body, said piston being slidable towards the container to a position in which it puts said pump chamber into communication with the container via said passage;
   wherein the pump further includes:
   a push rod including a central channel in which a valve seat is formed, said push rod sliding through said central opening in the end wall of the pump body, and said push rod being in contact with the pump body around a circular periphery having a second diameter D1 that is smaller than said first diameter D2; pusher means for displacing said push rod within said pump body toward said container;
   a punch secured to the piston and extending along said central channel of the push rod and being suitable for bearing in sealed manner against the valve seat;
   a support secured to the pump body and disposed at the end thereof adjacent to the container; and
   resilient bearing against the support means and urging the piston towards the end wall of the pump body.

2. A device according to claim 1, wherein the resilient means is disposed inside a spring chamber isolated from the container and delimited by: the support; a cylindrical wall secured to said support; and a portion of the piston sliding in sealing contact with said cylindrical wall when the piston slides in the pump body.

3. A device according to claim 1, wherein the resilient means is disposed at an end of the container distant from the piston, said resilient means is isolated from said container by a partition, and said resilient means applies thrust to the piston by means of a rod which passes through the container and slides in sealed manner through the partition.

4. A device according to claim 1, wherein the container includes a cylindrical wall through which the piston slides freely in such manner that the volume of said container reduces as the substance it contains is consumed.

5. A device according to claim 1, wherein the container includes a flexible wall enabling the volume of said container to reduce when the substance it contains is consumed.

6. A device according to claim 1, including an eyepiece attached to the pusher means and adapted to be pressed around the periphery of the eye of a user so as to adjust the distance between the eye and an outlet end of said device, and in such a manner as to center the device relative to the eye.

7. A device according to claim 1, wherein the pump body includes a first cylindrical wall close to the container of substance, said first cylindrical wall having the diameter D2 and receiving the piston, and a second cylindrical wall close to the end wall of said pump body, said second cylindrical wall having said diameter D1 smaller than the diameter D2, and wherein a radial flange of the push rod slides in sealed manner inside said second cylindrical wall.

* * * * *